US012779233B2

(12) United States Patent
Shelton et al.

(10) Patent No.: US 12,779,233 B2
(45) Date of Patent: Nov. 3, 2026

(54) SYSTEM AND METHOD FOR DETERMINING AND ALERTING A PATIENT TO A LOW BATTERY CONDITION IN AN IMPLANTABLE PULSE GENERATOR (IPG)

(71) Applicant: THE ALFRED E. MANN FOUNDATION FOR SCIENTIFIC RESEARCH, Valencia, CA (US)

(72) Inventors: Brian Shelton, Ventura, CA (US); Jeffrey Brydle, Pasadena, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 321 days.

(21) Appl. No.: 18/535,694

(22) Filed: Dec. 11, 2023

(65) Prior Publication Data

US 2024/0189610 A1 Jun. 13, 2024

Related U.S. Application Data

(60) Provisional application No. 63/387,169, filed on Dec. 13, 2022.

(51) Int. Cl.
*A61N 1/378* (2006.01)
*A61N 1/02* (2006.01)
*A61N 1/372* (2006.01)

(52) U.S. Cl.
CPC ............. *A61N 1/378* (2013.01); *A61N 1/025* (2013.01); *A61N 1/37258* (2013.01)

(58) Field of Classification Search
None
See application file for complete search history.

(56) References Cited

U.S. PATENT DOCUMENTS

2009/0182517 A1* 7/2009 Gandhi ................ A61B 5/0084 324/426
2011/0037475 A1* 2/2011 Ho ....................... G01R 31/389 324/427

(Continued)

OTHER PUBLICATIONS

International Search Report for International Application No. PCT/US2023/083410 dated Apr. 23, 2024, 3 pages.

(Continued)

*Primary Examiner* — Mallika D Fairchild
(74) *Attorney, Agent, or Firm* — Womble Bond Dickinson US LLP

(57) ABSTRACT

A method of operating an implantable pulse generator implanted in a patient includes determining, by a processor of the implantable pulse generator, that the patient has awoken; determining, by the processor of the implantable pulse generator, an average daily voltage depletion of a battery in the implantable pulse generator per day over a period of time in response to the patient being awake; determining, by the processor of the implantable pulse generator, a current voltage of the battery in the implantable pulse generator; determining, by the processor of the implantable pulse generator, a depletion voltage of the battery of the implantable pulse generator associated with the battery being depleted; and transmitting, from the implantable pulse generator to an electronic device remote from the implantable pulse generator, an alert in response to the current voltage being less than a sum of the average voltage depletion and the depletion voltage.

17 Claims, 5 Drawing Sheets

(56) References Cited

U.S. PATENT DOCUMENTS

| | | | | |
|---|---|---|---|---|
| 2013/0165819 | A1* | 6/2013 | Tieu | A61N 1/37252 600/595 |
| 2021/0001129 | A1* | 1/2021 | Pei | A61N 1/3708 |
| 2021/0216126 | A1 | 7/2021 | Dearman | |
| 2022/0199218 | A1 | 6/2022 | Rosinko et al. | |

OTHER PUBLICATIONS

Written Opinion for International Application No. PCT/US2023/083410 dated Apr. 23, 2024, 4 pages.

* cited by examiner

SYSTEM AND METHOD FOR DETERMINING AND ALERTING A PATIENT TO A LOW BATTERY CONDITION IN AN IMPLANTABLE PULSE GENERATOR (IPG)

CROSS-REFERENCE TO RELATED APPLICATION(S)

The present application claims priority to and the benefit of U.S. Provisional Application No. 63/387,169, filed Dec. 13, 2022, the entire content of which is incorporated herein by reference.

BACKGROUND

1. Field

The present disclosure relates to various systems and methods for determining and alerting a patient to a low battery condition in an implantable pulse generator.

2. Description of the Related Art

Implantable pulse generators (IPGs) are used for a variety of therapeutic treatments in a patient, such as neurostimulation, cardiac stimulation, and/or spinal cord stimulation. IPGs include an onboard rechargeable battery that should be periodically recharged. Failure to alert the patient with sufficient advance notice before the battery is depleted may result in serious possible adverse health consequences.

The above information disclosed in this Background section is only for enhancement of understanding of the background of the invention and therefore it may contain information that does not constitute prior art.

SUMMARY

The present disclosure relates to various embodiments of a method for determining and alerting a patient to a low battery condition in an implantable pulse generator (IPG). In one embodiment, a method of operating an implantable pulse generator implanted in a patient includes determining, by at least one processor of the implantable pulse generator, that the patient has awoken; determining, by the processor(s) of the implantable pulse generator, an average daily voltage depletion of a battery in the implantable pulse generator per day over a period of time in response to the determining that the patient has awoken; determining, by the processor(s) of the implantable pulse generator, a current voltage of the battery in the implantable pulse generator; determining, by the processor(s) of the implantable pulse generator, a depletion voltage of the battery of the implantable pulse generator associated with the battery being depleted; and transmitting, from the implantable pulse generator to an electronic device remote from the implantable pulse generator, an alert in response to the current voltage being less than a sum of the average voltage depletion and the depletion voltage.

In another embodiment, the method includes determining, by at least one processor of the implantable pulse generator, an average daily voltage depletion of a battery in the implantable pulse generator per day at a set time of day; determining, by the processor(s) of the implantable pulse generator, a current voltage of the battery in the implantable pulse generator; determining, by the processor(s) of the implantable pulse generator, a depletion voltage of the battery of the implantable pulse generator associated with the battery being depleted; and transmitting, from the implantable pulse generator to an electronic device remote from the implantable pulse generator, an alert in response to the current voltage being less than a sum of the average daily voltage depletion and the depletion voltage.

The present disclosure also relates to various embodiments of a method of operating an implantable pulse generator implanted in a patient. In one embodiment, the method includes determining, by at least one processor of the implantable pulse generator, that the patient has awoken, and determining, by the processor(s) of the implantable pulse generator, a current voltage of a battery in the implantable pulse generator in response to the determining that the patient has awoken. The method also includes determining, by the processor(s) of the implantable pulse generator, a current battery fill capacity percentage of the battery corresponding to the current voltage, and determining, by the processor(s) of the implantable pulse generator, an average fill capacity percentage drop of the battery per day over a period of time. The method further includes determining, by the processor(s) of the implantable pulse generator, a low battery voltage corresponding to the average fill capacity percentage drop, and transmitting, from the implantable pulse generator to an electronic device remote from the implantable pulse generator, an alert in response to the current voltage being less than the low battery voltage.

In another embodiment, the method includes determining, by at least one processor of the implantable pulse generator, a current voltage of a battery in the implantable pulse generator at a set time of day; determining, by the processor(s) of the implantable pulse generator, a current battery fill capacity percentage of the battery corresponding to the current voltage; determining, by the processor(s) of the implantable pulse generator, an average fill capacity percentage drop of the battery per day over a period of time; determining, by the processor(s) of the implantable pulse generator, a low battery voltage corresponding to the average fill capacity percentage drop; and transmitting, from the implantable pulse generator to an electronic device remote from the implantable pulse generator, an alert in response to the current voltage being less than the low battery voltage.

The present disclosure also relates to various embodiments of an implantable pulse generator configured to be implanted in a patient. In one embodiment, the implantable pulse generator includes a processor, a non-volatile memory device, a communications device, a power supply, and an inertial measurement unit. The non-volatile memory device comprises instructions stored therein which, when executed by the processor, cause the processor to determine the patient is awake, determine a current voltage of the power supply in response to the patient being awake, determine an average daily voltage depletion of the power supply, and transmit an alert in response to the current voltage minus the average daily voltage depletion being less than a depletion voltage of the power supply.

The present disclosure also relates to various embodiments of a system for operating an implantable pulse generator implanted in a patient. In one embodiment, the system includes means for determining, by a processor of the implantable pulse generator, that the patient has awoken, means for determining, by the processor of the implantable pulse generator, an average voltage depletion of a battery in the implantable pulse generator per day in response to the determining that the patient has awoken, means for determining, by the processor of the implantable pulse generator, a current voltage of the battery in the implantable pulse generator, means for determining, by the processor of the implantable pulse generator, a depletion voltage of the battery of the implantable pulse generator associated with the battery being depleted, and means for transmitting, from the implantable pulse generator to an electronic device remote from the implantable pulse generator, an alert in response to the current voltage being less than a sum of the average voltage depletion and the depletion voltage. In another embodiment, the system includes means for determining, by a processor of the implantable pulse generator, that the patient has awoken, means for determining, by the processor of the implantable pulse generator, a current voltage of a battery in the implantable pulse generator in response to the determining that the patient has awoken, means for determining, by the processor of the implantable pulse generator, a current battery fill capacity percentage of the battery corresponding to the current voltage, means for determining, by the processor of the implantable pulse generator, an average fill capacity percentage drop of the battery per day over a period of time, means for determining, by the processor of the implantable pulse generator, a low battery voltage corresponding to the average fill capacity percentage drop, and means for transmitting, from the implantable pulse generator to an electronic device remote from the implantable pulse generator, an alert in response to the current voltage being less than the low battery voltage.

This summary is provided to introduce a selection of features and concepts of embodiments of the present disclosure that are further described below in the detailed description. This summary is not intended to identify key or essential features of the claimed subject matter, nor is it intended to be used in limiting the scope of the claimed subject matter. One or more of the described features or tasks may be combined with one or more other described features or tasks to provide a workable device or method.

BRIEF DESCRIPTION OF THE DRAWINGS

The features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale.

DETAILED DESCRIPTION

Figure 1A:
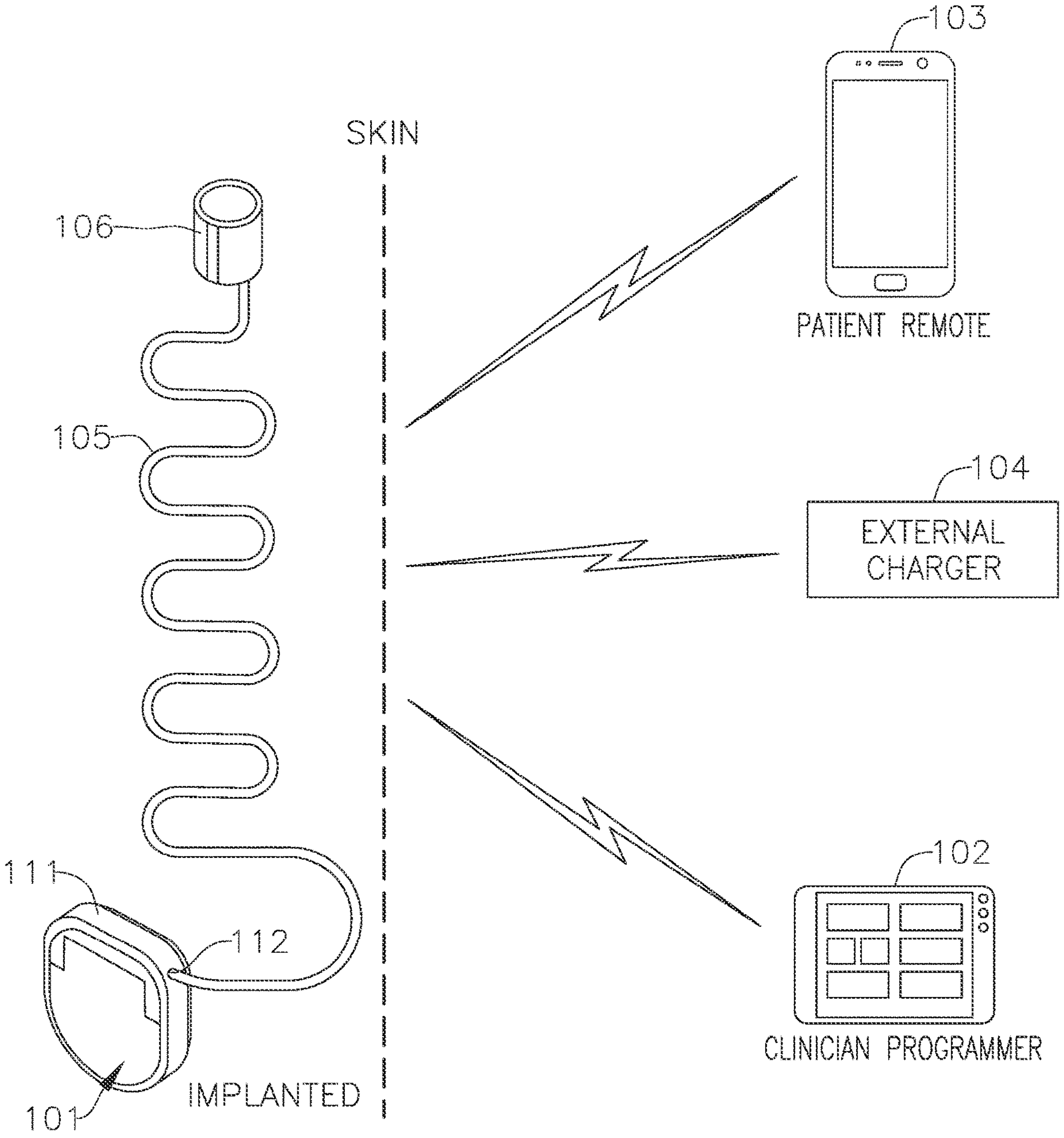
FIG. 1A is a schematic view of a stimulation system including an implantable pulse generator (IPG), a clinician programmer (CP) device, a patient remote (PR) device, and an external charger according to one embodiment of the present disclosure.

The present disclosure relates to various systems and methods of determining that a battery in an implantable pulse generator (IPG) implanted in a patient needs to be recharged. For instance, in one or more embodiments, the systems and methods of the present disclosure may alert the patient in the morning (e.g., upon waking) if the battery of the IPG does not have sufficient charge to remain charged throughout the coming day and night. The systems and methods of the present disclosure may be utilized for IPG batteries that exhibit linear (or substantially linear) discharge characteristics and for IPG batteries that exhibit non-linear discharge characteristics. The systems and methods of the present disclosure may be configured to determine that the battery needs to be recharged based on the following: (i) a comparison of an average daily voltage depletion for the battery to the current voltage of the battery; (ii) a comparison of the average daily voltage depletion for the battery, plus one or more standard deviations from the average, to the current voltage of the battery; (iii) a comparison of an average daily voltage depletion for the battery, adjusted by a factor representing a change in the charge delivered by the IPG due to a change in one or more therapeutic parameters of the IPG, to the current voltage of the battery; (iv) a comparison of an average daily voltage depletion for the battery, adjusted by a factor representing a change in the total energy consumed by the IPG due to a change in one or more therapeutic parameters of the IPG, to the current voltage of the battery; or (iv) a comparison of the average depletion of the battery capacity per day, determined by referencing a table correlating a number of different battery voltages with a number of corresponding percent capacities of the battery, to the current battery capacity of the battery. In this manner, the systems and methods of the present disclosure ensure that the battery has sufficient charge to last throughout the night when the patient is unlikely to notice a low battery alert, and thereby prevent (or at least mitigate against) a catastrophic medical event due to the IPG powering off during the night.

The terminology utilized herein is for the purpose of describing particular embodiments only and is not intended to be limiting of the present disclosure. As utilized herein, the singular forms “a”, “an” and “the” are intended to include the plural forms as well, unless the context clearly indicates otherwise. As utilized herein, the term “and/or” includes any and all combinations of one or more of the associated listed items.

It will be understood that, although the terms “first”, “second”, “third”, etc., may be utilized herein to describe one or more suitable elements, components, regions, and/or sections, these elements, components, regions, and/or sections should not be limited by these terms. These terms are only utilized to distinguish one element, component, region, layer or section from another element, component, region, layer or section. Thus, a first element, component, region, or section discussed could be termed a second element, component, region, or section, without departing from the spirit and scope of the present disclosure.

It will be understood that when an element is referred to as being “on”, “connected to”, “coupled to”, or “adjacent to” another element, it can be directly on, connected to, coupled to, or adjacent to the other element, or one or more intervening element(s) may be present. In contrast, when an element is referred to as being “directly on,” “directly connected to”, “directly coupled to”, or “immediately adjacent to” another element, there are no intervening elements present.

As utilized herein, the term “substantially” and similar terms are utilized as terms of approximation and not as terms of degree, and are intended to account for the inherent deviations in measured or calculated values that would be recognized by those of ordinary skill in the art. Also, the terms "about," "approximately," and similar terms, when utilized herein in connection with a numerical value or a numerical range, are inclusive of the stated value and refer to within an acceptable range of deviation for the particular value as determined by one of ordinary skill in the art, considering the measurement in question and the error associated with measurement of the particular quantity (e.g., the limitations of the measurement system).

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Example embodiments of the present disclosure will now be described with reference to the accompanying drawings. In the drawings, the same or similar reference numerals refer to the same or similar elements throughout. As utilized herein, the utilize of the term "may," when describing embodiments of the present disclosure, refers to "one or more embodiments of the present disclosure."

Figure 1B:
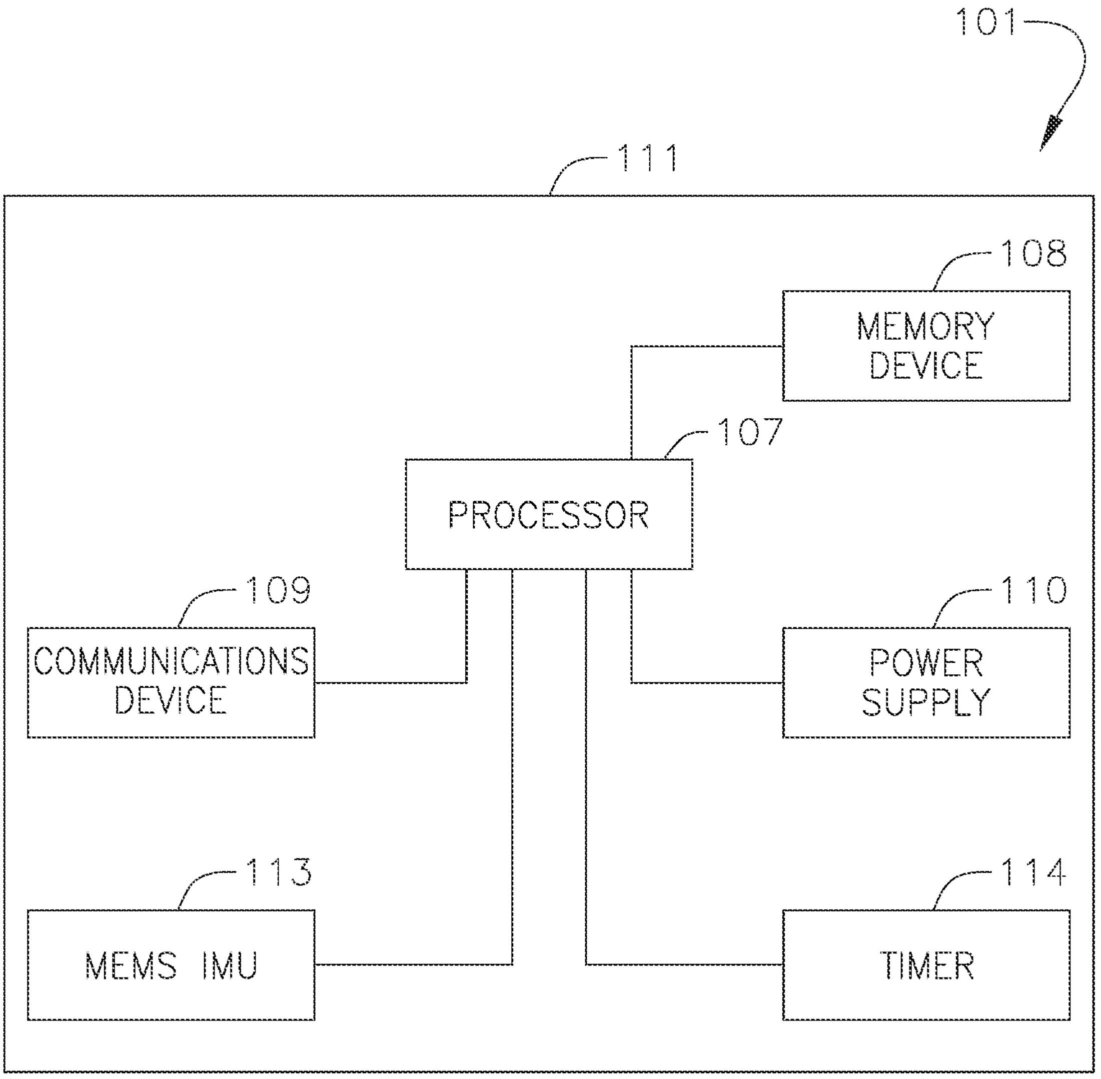
FIG. 1B is a schematic block diagram of the IPG according to the embodiment illustrated in FIG. 1A.

FIGS. 1A-1B are schematic views of a stimulation system 100 configured to treat a patient via electrical stimulation, such as neurostimulation, cardiac stimulation, or spinal cord stimulation. Stimulation system 100 includes an implantable pulse generator (IPG) 101 implanted in a patient, a clinician programmer (CP) device 102 and a patient remote (PR) device 103 each electronically coupled to (i.e., in wireless RF communication with) the IPG 101, and an external charger 104 configured to charge the IPG via inductive coupling. The system 100 also includes at least one electrical lead 105 connected to the IPG 101. Each of the electrical leads 105 includes an electrode 106 (e.g., a cuff electrode, a cardiac electrode, or a spinal cord paddle at a distal end of the electrical lead 105) to periodically deliver an electric current pulse for a variety of therapeutic treatments for the patient, such as neurostimulation, cardiac stimulation, and/or spinal cord stimulation. The type or kind of the electrode 106 may be selected based on the location and the type nerves stimulated (e.g., a cuff electrode to stimulate a nerve bundle, such as the hypoglossal nerve or the vagus nerve; a cardiac electrode to stimulate heart/myocardium; or a spinal cord lead, such as a paddle or a linear lead, to stimulate the spinal cord). The IPG 101 and the electrical leads 105 may be implanted in any suitable locations in the patient depending on the therapeutic treatment delivered by the system 100. For example, the IPG 101 may be implanted in a subcutaneous pocket in the upper chest of the patient, and the electrical leads 105 may extend from the IPG 101 through the superior vena cava such that the electrodes 106 are connected to the myocardium of the patient's heart. In one or more embodiments, the IPG 101 may be an obstructive sleep apnea (OSA) stimulator device.

In the embodiment illustrated in FIG. 1B, the IPG 101 includes a processor (e.g., a processing circuit) 107, a non-volatile memory device 108 (e.g., flash memory), a communications device 109 (e.g., a receiver and a transmitter, or a transceiver), and a power supply 110 (e.g., a primary battery or an inductively chargeable rechargeable battery). The communications device 109 provides wireless communication links through the skin of the patient to the CP device 102 and the PR device 103. Wireless links may include Bluetooth™, Bluetooth Low Energy or other protocols with suitable authentication and encryption to protect patient data. In one or more embodiments, the non-volatile memory device 108, the communications device 109, and the power supply 110 are in communication with each other over the processor 107. Additionally, in the illustrated embodiment, the processor 107, the non-volatile memory device 108, the communications device 109, and the power supply 110 are housed in a housing or a case 111, and proximal end portions of the electrical leads 105 extend through opening(s) 112 in the case (e.g., housing) 111 and are connected to dedicated circuitry that provides stimulation pulses as controlled by the processor 107.

In the illustrated embodiment, the IPG 101 also includes a micro-electro-mechanical system (MEMS) inertial measurement unit (IMU) 113 configured to determine (e.g., measure or calculate) the orientation of the IPG 101. In one or more embodiments, the MEMS IMU 113 may include one or more accelerometers (e.g., 3-axis accelerometer), a gyroscope (e.g., a 3-axis gyroscope), and/or a magnetometer (e.g., a 3-axis magnetometer). In the illustrated embodiment, the IPG 101 also includes a timer 114 (e.g., a real-time clock (RTC)) configured to measure the passage of time. The MEMS IMU 113 and the timer 114 may be in communication with the processor 107, the non-volatile memory device 108, the communications device 109, and the power supply 110.

As used herein, the term "processor" includes any combination of hardware, firmware, memory and software, employed to process data, digital signals, and/or analog signals such as voltage levels. The hardware of a controller may include, for example, a microcontroller, application specific integrated circuits (ASICs), general purpose or special purpose central processors (CPUs), digital signal processors (DSPs), graphics processors (GPUs), and programmable logic devices such as field programmable gate arrays (FPGAs). In a processor, as utilized herein, each function is performed either by hardware configured, i.e., hard-wired, to perform that function, or by more general purpose hardware, such as a CPU, configured to execute instructions stored in a non-transitory storage medium or memory. A processor may contain two or more processors, for example, a processor may include two processors, an FPGA and a CPU, interconnected on a PCB.

The memory device 108 of the IPG 101 includes instructions, which, when executed by the processor 107, cause the processor 107 to determine that the patient has awoken. In one or more embodiments, the instructions stored in the memory device are configured to determine that the patient has awoken in response to the measurements or calculations from the MEMS IMU 113 indicating that the IPG 101 is oriented vertically (or substantially vertically) for a threshold duration, as determined by the timer (e.g., clock) 114. In one or more embodiments, the threshold duration may be in a range from approximately (e.g., about) 1 minute to approximately 45 minutes. In one embodiment, the threshold duration may be approximately 30 minutes. The threshold duration is configured to mitigate against false positive determinations that the patient has awoken, such as when the patient briefly gets up during the night to use the restroom.

Otherwise, determining that the patient has awoken only in response to the orientation of the IPG 101 determined by the MEMS IMU 113 may result in a false determination.

In one or more embodiments, the memory device 108 stores historical statistical data, including a distribution of times when the patient has awoken over a period of days, weeks, or months. For instance, in one or more embodiments, the memory device 108 may store a lookup table including the patient wakeup time for each day in a period of time, such as a period of several days to a month or more. In one or more embodiments, the memory device 108 may store a mean or median wakeup time over the period of days, weeks, or months. In one or more embodiments, the memory device 108 includes instructions which, when executed by the processor 107, cause the processor 107 to determine that the patient has awoken in response to measurements or calculations by the MEMS IMU 113 indicating that the IPG 101 is oriented vertically (or substantially vertically) and the current time, as determined by the timer (e.g., the real-time clock) 114, is within a threshold deviation of the mean or median wakeup time. In one or more embodiments, the threshold deviation may be a standard deviation of the wakeup times stored in the memory device 108. In one or more embodiments, the threshold deviation may be a set value, for example, 15 minutes, 30 minutes, or 45 minutes. For instance, in one or more embodiments, the instructions stored in the memory device 108, when executed by the processor 107, cause the processor 107 to determine that the patient has awoken in response to the measurements or calculations by the MEMS IMU 113 indicating that the IPG 101 is vertical (or substantially vertical) within approximately 30 minutes of the mean or median wakeup time stored in the memory device 108.

The instructions stored in the memory device 108 are also configured to determine (e.g., calculate or measure) if the power supply 110 does not have sufficient charge to power the IPG 101 for the remainder of the day and throughout the night. In the illustrated embodiment, the instructions stored in the memory device 108, when executed by the processor 107, cause the processor 107 to determine (e.g., measure or calculate) the current voltage of the power supply 110 in response to the determination that the patient has awoken. Additionally, in one or more embodiments, the instructions stored in the memory device are configured to calculate or determine the daily voltage drop of the power supply 110 and to compare the current voltage of the power supply 110, less the daily voltage drop (or a factor based thereon), to a low state of charge of the power supply 110. For instance, in one or more embodiments, the low state of charge of the power supply 110 may be approximately 3.0V. In one or more embodiments, the low state of charge of the power supply 110 may be in a range from approximately 3.0V to approximately 3.3V. In one or more embodiments, the low state of charge of the power supply 110 may be the minimum voltage level (or just below the minimum voltage level) required to deliver pulses through the electrode(s) 106, such as approximately 3.3V. Various methods for determining that the power supply 110 has insufficient charge to power the IPG 101 throughout the remainder of the day and throughout the night are described below in more detail.

Additionally, in one or more embodiments, the instructions stored in the memory device 108, when executed by the processor 107, cause the IPG 101 to transmit an alert, via the communications device 109, to the PR device 103 in response to the determination that the current voltage of the power supply 110 (determined in response to the patient awakening), less the daily voltage drop (or a factor based thereon), is equal (or substantially equal) or less than the voltage corresponding to the low state of charge of the power supply 110 (e.g., approximately 3.0V). The alert is configured to signal to the patient that the IPG 101 needs to be recharged. The alert may be any suitable type or kind of alert, such as an audio alert (e.g., a chime) played from a speaker of the PR device 103, a visual alert (e.g., a textual message) displayed on a display of the PR device 103, a tactile alert (e.g., vibrations) generated by the PR device 103, or any combination thereof.

Notifying the patient, when the patient awakens, that the power supply 110 has insufficient charge to power the IPG 101 throughout the remainder of the day provides the patient with adequate time before the patient goes to bed to charge the power supply 110 of the IPG 101 (at the patient's convenience) with the external charger 104 via inductive charging.

Figure 2:
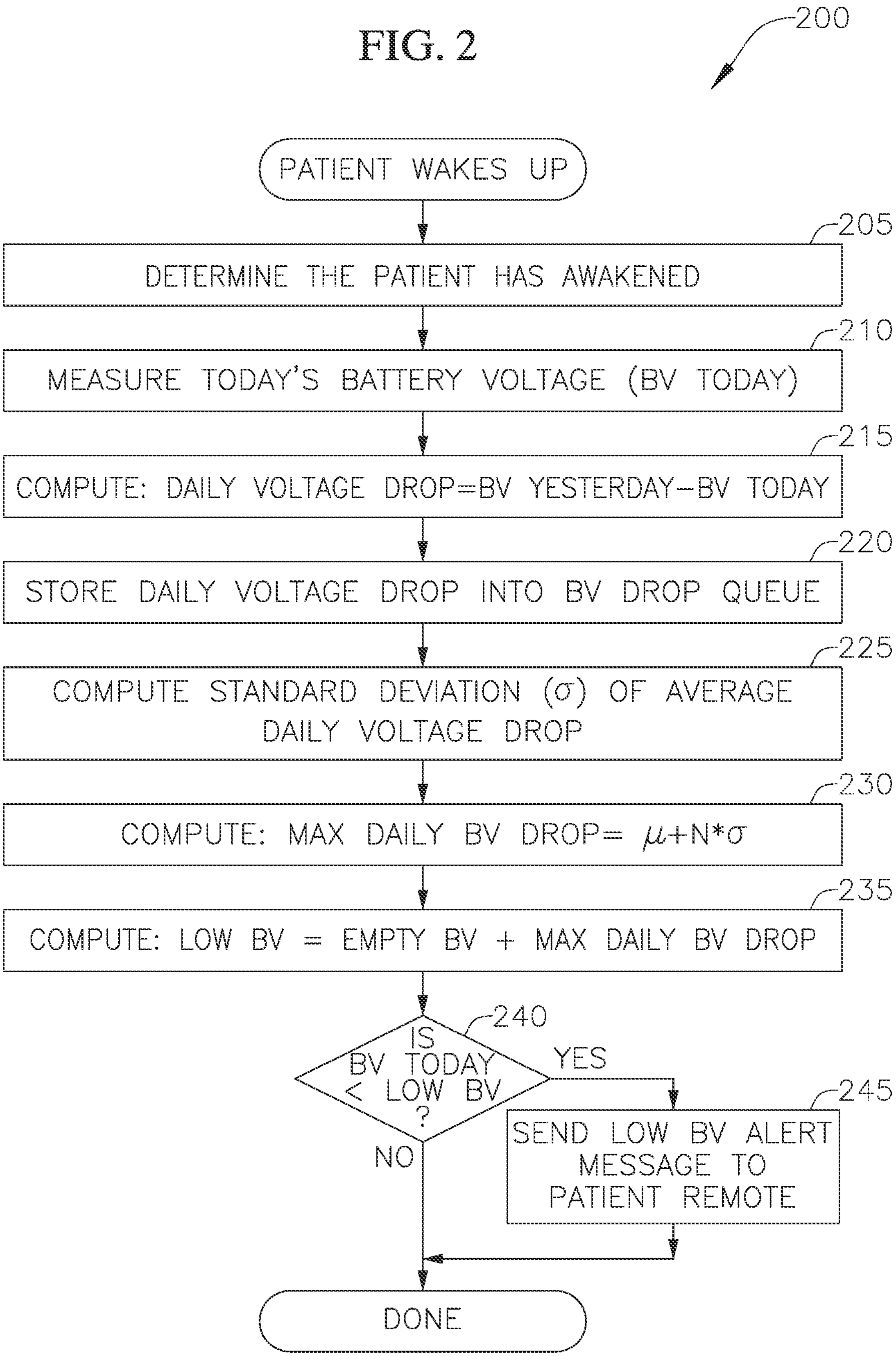
FIG. 2 is a flowchart illustrating tasks of a method of determining and signaling that the battery of an implantable pulse generator (IPG) is low according to an embodiment of the present disclosure in which the battery has linear discharge characteristics.

FIG. 2 depicts a flowchart illustrating tasks of a method 200 of determining and signaling that the battery of an implantable pulse generator (IPG) (e.g., the embodiment of the IPG 101 depicted in FIG. 1) is low according to one embodiment of the present disclosure. In one or more embodiments, the method 200 may be applied in an embodiment in which the battery of the IPG has linear (or substantially linear) discharge characteristics.

In the illustrated embodiment, the method 200 includes a task 205 of determining (e.g., calculating) that the patient has awoken. The task 205 may include determining, utilizing a micro-electro-mechanical system (MEMS) inertial measurement unit (IMU) of the IPG, that the IPG is oriented vertically (or substantially vertically) for a threshold duration, as determined by a clock (e.g., a real-time clock (RTC)) of the IPG. In one or more embodiments, the threshold duration may be in a range from approximately 1 minute to approximately 45 minutes (e.g., approximately 30 minutes). The threshold duration is configured to mitigate against false positive determinations that the patient has awoken, such as when the patient briefly gets up for a drink or to use the restroom. Otherwise, determining that the patient has awoken only in response to the orientation of the IPG determined by the MEMS IMU may result in a false determination.

In one or more embodiments, the task 205 may include determining, utilizing the MEMS IMU of the IPG, that the IPG is oriented vertically (or substantially vertically) at a time within a threshold deviation of the average wakeup time of the patient (e.g., the average wakeup time±.a threshold deviation) In one or more embodiments, the task 205 may include referencing the mean or median wakeup time of the patient stored in the memory device of the IPG, or the task 205 may include calculating the mean or median wakeup time of the patient from a lookup table stored in the memory device of the IMU that contains historical statistics listing the wakeup time of the patient for each of plurality of days in the past (e.g., Day 1: Wakeup Time 8:45 am; Day 2: Wakeup Time 8:36 am; and Day 3: Wakeup Time 8:51 am). In one or more embodiments, the threshold deviation may be a set value, for example, 15 minutes, 30 minutes, or 45 minutes. For instance, in one or more embodiments, task 205 may include determining that the patient has awoken in response to the MEMS IMU indicating that the IPG is oriented vertical (or substantially vertical) at a time within a range from approximately 8:15 am to approximately 8:45 am (i.e., 8:30 am±15 minutes). Referencing the patient's average wakeup time is configured to mitigate against false positive determinations that the patient has awoken, such as when the patient gets up during the night for a drink or to use the restroom. Otherwise, determining that the patient has awoken only in response to the orientation of the IPG determined by the MEMS IMU may result in a false determination.

In the illustrated embodiment, the method 200 includes a task 210 of determining (e.g., calculating or measuring) the current battery voltage (BVtoday) of the battery in the IPG in response to the determination in task 205 that the patient has awoken (e.g., in the morning). Determining (in task 210) the current battery voltage of the IPG in response to the patient awakening, and the subsequent tasks of alerting the patient if the battery voltage is low, provides the patient with adequate time before the patient goes to bed to charge the power supply of the IPG at the patient's convenience.

In the illustrated embodiment, the method 200 also includes a task 215 of determining (e.g., calculating or measuring) the average daily voltage drop (μ) of the battery voltage over a period of time, such as a week or longer. For instance, in one or more embodiments, the task 215 may include a task of determining the average daily voltage drop (μ) of the battery voltage over a period of time immediately preceding the time at which the task 210 is performed to determine the current battery voltage.

In the illustrated embodiment, the method 200 also includes a task 220 of storing the average daily voltage drop (μ) of the battery, determined in task 215, in a queue (BVDropQueue) in a memory device of the IPG or an external electronic device.

In the illustrated embodiment, the method 200 includes a task 225 of determining (e.g., calculating or measuring) the standard deviation (o) of the average daily voltage drop (μ), determined in task 215, over the period of time utilized in task 215 (e.g., a week or longer).

In the illustrated embodiment, the method 200 also includes a task 230 of determining (e.g., calculating) the maximum daily voltage drop (MaxDailyBV Drop) of the battery in the IPG according to Equation 1 as follows:

$$\text{MaxDailyBVDrop}=\mu+N*\sigma \quad \text{(Equation 1)}$$

wherein μ is the average daily voltage drop of the battery, N is an integer, and σ is the standard deviation of the average daily voltage drop μ. Increasing the integer N increases the determination of the maximum daily voltage drop (MaxDailyBVDrop) of the battery such that the method 200 is more conservative in alerting the user to a low battery condition. In one or more embodiments, the integer N may be 1, 2, 3, or more. In one or more embodiments, the integer N may be zero (0) such that the maximum daily voltage drop (MaxDailyBV-Drop) is equal to the average daily voltage drop (μ).

In the illustrated embodiment, the method 200 includes a task 235 of determining (e.g., computing or calculating) a low battery voltage (LowBV) according to Equation 2 as follows:

$$\text{LowBV}=\text{EmptyBV}+\text{MaxDailyBVDrop} \quad \text{(Equation 2)}$$

wherein EmptyBV is the voltage of the battery when the battery is near depletion (i.e., the battery has a capacity in a range from greater than 0% to approximately 10% fill), and MaxDailyBV Drop is the maximum daily voltage drop of the battery, as determined in task 230 with reference to Equation 1 above. The low battery voltage LowBV is the voltage of the battery at which the battery does not have (or potentially does not have) sufficient charge to power the IPG throughout the remainder of the day and the night.

In the illustrated embodiment, the method 200 also includes a task 240 of comparing the current battery voltage (BVtoday) determined in task 205 to the low battery voltage (LowBV) determined in task 235 according to Equation 2 above.

The method 200 also includes a task 245 of generating an alert (e.g., sending a message from the IPG to a patient remote device) in response to the current battery voltage (BVtoday) determined in task 205 being equal to or less than the low battery voltage (LowBV) determined in task 235. The alert generated in task 245 may be any suitable type or kind of alert, such as an audio alert (e.g., a chime), a visual alert (e.g., a textual message), a tactile alert (e.g., haptic feedback), or any combination thereof.

In response to the current battery voltage (BVtoday) determined in task 205 being greater than the to the low battery voltage (LowBV), the task 245 is not performed and the method returns to task 205 the next time the patient awakens (e.g., the next day).

Figure 3:
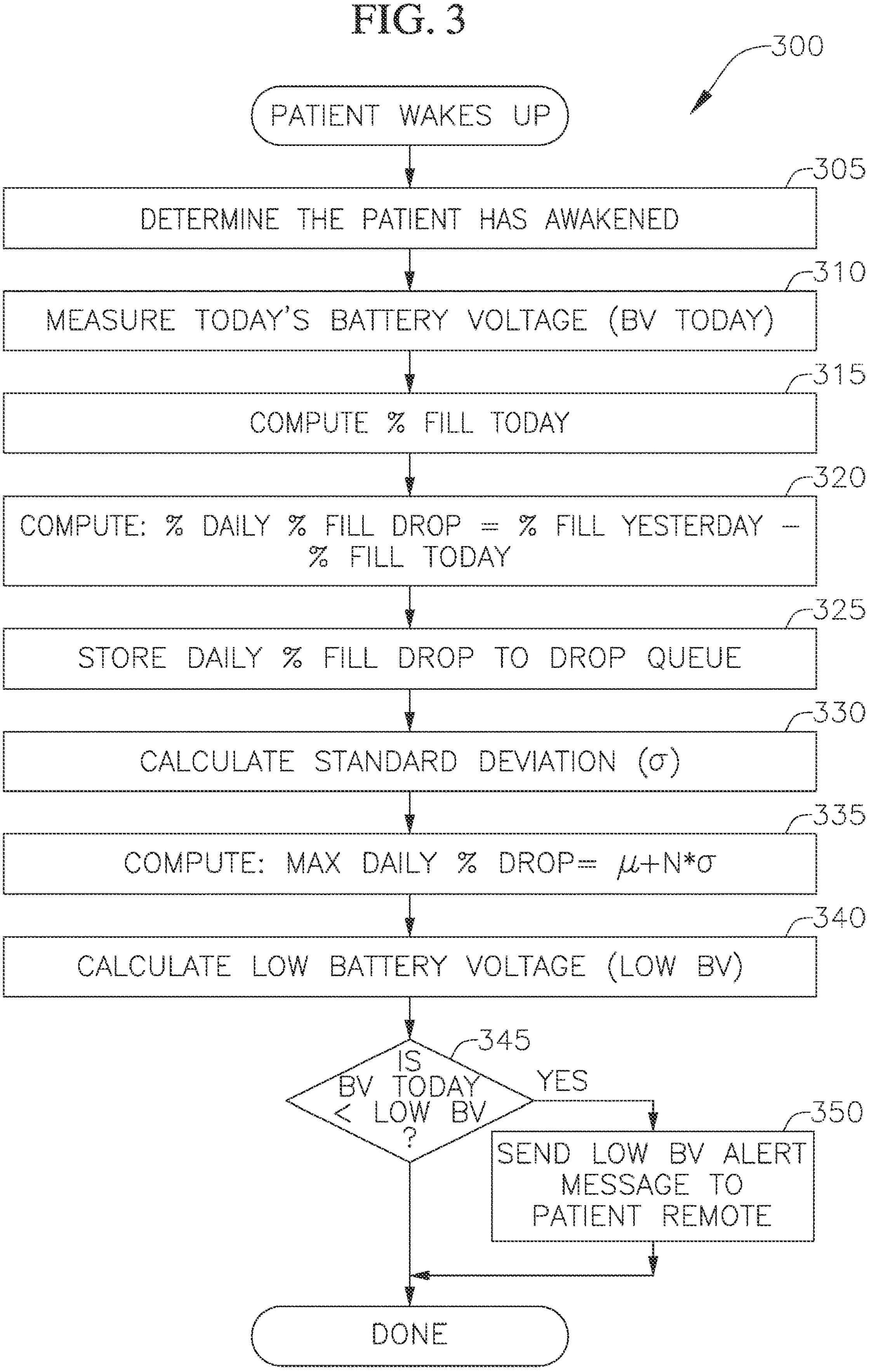
FIG. 3 is a flowchart illustrating tasks of a method of determining and signaling that the battery of an implantable pulse generator (IPG) is low according to an embodiment of the present disclosure in which the battery has non-linear discharge characteristics.

FIG. 3 depicts a flowchart illustrating tasks of a method 300 of determining and signaling that the battery of an implantable pulse generator (IPG) is low according to one embodiment of the present disclosure. In one or more embodiments, the method 300 may be applied in an embodiment in which the battery of the IPG has non-linear discharge characteristics.

In the illustrated embodiment, the method 300 includes a task 305 of determining (e.g., calculating) that the patient has awoken. The task 305 may include determining, utilizing a micro-electro-mechanical system (MEMS) inertial measurement unit (IMU) of the IPG, that the IPG is oriented vertically (or substantially vertically) for a threshold duration, as determined by a clock (e.g., a real-time clock (RTC)) of the IPG. In one or more embodiments, the threshold duration may be in a range from approximately 1 minute to approximately 45 minutes (e.g., approximately 30 minutes). The threshold duration is configured to mitigate against false positive determinations that the patient has awoken, such as when the patient briefly gets up for a drink or to use the restroom. Otherwise, determining that the patient has awoken only in response to the orientation of the IPG determined by the MEMS IMU may result in a false determination.

In one or more embodiments, the task 305 may include determining, utilizing the MEMS IMU of the IPG, that the IPG is oriented vertically (or substantially vertically) at a time within a threshold deviation of the average wakeup time of the patient (e.g., the average wakeup time ±.a threshold deviation) In one or more embodiments, the task 305 may include referencing the mean or median wakeup time of the patient stored in the memory device of the IPG, or the task 305 may include calculating the mean or median wakeup time of the patient from a lookup table stored in the memory device of the IMU that contains historical statistics listing the wakeup time of the patient for each of plurality of days in the past (e.g., Day 1: Wakeup Time 8:45 am; Day 2: Wakeup Time 8:36 am; and Day 3: Wakeup Time 8:51 am). In one or more embodiments, the threshold deviation may be a set value, for example, 15 minutes, 30 minutes, or 45 minutes. For instance, in one or more embodiments, task 305 may include determining that the patient has awoken in response to the MEMS IMU indicating that the IPG is oriented vertical (or substantially vertical) at a time within a range from approximately 8:15 am to approximately 8:45 am (i.e., 8:30 am±15 minutes). Referencing the patient's average wakeup time is configured to mitigate against false positive determinations that the patient has awoken, such as when the patient gets up during the night for a drink or to use the restroom. Otherwise, determining that the patient has awoken only in response to the orientation of the IPG determined by the MEMS IMU may result in a false determination.

In the illustrated embodiment, the method 300 includes a task 310 of determining (e.g., calculating or measuring) the current battery voltage (BVtoday) of the battery in the IPG in response to the determination in task 305 that the patient has awoken (e.g., in the morning). Determining (in task 310) the current battery voltage of the IPG in response to the patient awakening, and the subsequent tasks of alerting the patient if the battery voltage is low, provides the patient with adequate time before the patient goes to bed to charge the power supply of the IPG at the patient's convenience.

In the illustrated embodiment, the method 300 also includes a task 315 of determining the current percent capacity (% FillToday) of the battery corresponding to the current battery voltage (BVtoday) determined in task 310. In one or more embodiments, the task 315 may be performed by referencing a map or a table, stored in the firmware of the IPG. In one or more embodiments, the table lists a plurality of battery voltages BV1-BV10 (e.g., a plurality of battery voltages spaced at regular, or substantially regular, intervals) and a plurality of corresponding battery capacity percentages, as shown for example in Table 1 below. Although the table below lists ten (10) battery voltages BV and ten corresponding battery capacities (%), in one or more embodiments the table may store any other suitable number of battery voltages BV and corresponding battery capacities, such as, for example, in a range from 5 to 20 battery voltages BV and corresponding battery capacities (%). In one or more embodiments in which the current battery voltage (BVtoday) does not match one of the battery voltages BV listed in the table, the task 315 includes using interpolation (e.g., linear interpolation) to determine the current percent capacity of the battery corresponding to the current battery voltage (BVtoday). For instance, in one or more embodiments in which the current battery voltage (BVtoday) is between the battery voltage BV4 and the battery voltage BV5, the task 315 may include determining the current battery capacity (% FillToday) as follows:

$$\%\ FillToday = 40\% + (BVToday - BV4) * \frac{50\% - 40\%}{BV5 - BV4}.$$

In one or more embodiments, the task 315 may utilize any other suitable type of interpolation, such as polynomial interpolation or piecewise constant interpolation. In one or more embodiments, the table listing the battery voltages and the corresponding battery capacity percentages may be generated by utilizing a fixed resistor or a fixed current sink connected to the battery of the IPG to discharge battery, and regularly measuring (i.e., at a constant time interval) the battery voltage.

TABLE 1

| Battery Voltage (BV) | Battery Capacity (%) |
|---|---|
| BV1 | 10% fill |
| BV2 | 20% fill |
| BV3 | 30% fill |
| BV4 | 40% fill |
| BV5 | 50% fill |
| BV6 | 60% fill |
| BV7 | 70% fill |
| BV8 | 80% fill |

TABLE 1-continued

| Battery Voltage (BV) | Battery Capacity (%) |
|---|---|
| BV9 | 90% fill |
| BV10 | 100% fill |

In the illustrated embodiment, the method 300 also includes a task 320 of determining (e.g., calculating or measuring) the average daily capacity drop (μ) of the battery voltage over a period of time, such as a week or longer. For instance, in one or more embodiments, the task 320 may include a task of determining the average daily capacity drop (μ) of the battery voltage over a period of time immediately preceding the time at which the task 310 is performed to determine the current battery voltage (BVtoday) or the time at which task 315 is performed to determine the current percent capacity (% FillToday) (i.e., the trailing average battery capacity drop).

In the illustrated embodiment, the method 300 also includes a task 325 of storing the average daily capacity drop (μ) of the battery, determined in task 320, in a queue (BVDropQueue) in a memory device of the IPG or an external electronic device.

In the illustrated embodiment, the method 300 includes a task 330 of determining (e.g., calculating or measuring) the standard deviation (o) of the average daily battery capacity drop (μ) over the period of time utilized in task 320.

In the illustrated embodiment, the method 300 also includes a task 335 of determining (e.g., calculating) the maximum daily battery capacity drop (MaxDaily % Drop) of the battery in the IPG according to Equation 3 as follows:

$$\text{MaxDaily \% Drop} = \mu + N^{*}\sigma \qquad \text{(Equation 3)}$$

wherein μ is the average daily capacity drop of the battery, N is an integer, and σ is the standard deviation of the average daily capacity drop μ. Increasing the integer N increases the determination of the maximum daily capacity drop (MaxDaily % Drop) of the battery such that the method 300 is more conservative in alerting the user to a low battery condition. In one or more embodiments, the integer N may be 1, 2, 3, or more. In one or more embodiments, the integer N may be zero (0) such that the maximum daily capacity drop (MaxDaily % Drop) is equal to the average daily capacity drop (μ).

In the illustrated embodiment, the method 300 includes a task 340 of determining (e.g., computing or calculating) a low battery voltage (LowBV) at which the battery does not have sufficient charge to power the IPG throughout the remainder of the day and the night (e.g., a 24 hour period). In one or more embodiments, the task 340 may be performed by determining the battery voltage (BV) corresponding to the maximum daily capacity drop (MaxDaily % Drop) from Table 1 above. In one or more embodiments in which the maximum daily capacity drop (MaxDaily % Drop) is between two battery capacities (%) in Table 1, the task 340 may utilize interpolation (e.g., linear, polynomial, or piecewise constant) to determine the battery voltage (BV) corresponding to the maximum daily capacity drop (MaxDaily % Drop). For example, in one or more embodiments in which the maximum daily capacity drop (MaxDaily % Drop) is between 10% and 20%, the task 340 may include determining the low battery voltage (LowBV) utilizing linear interpolation as follows:

$$LowBV = BV1 + (MaxDaily\ \%\ Drop - 10\%) * \frac{BV2 - BV1}{20\% - 10\%}.$$

In the illustrated embodiment, the method 300 also includes a task 345 of comparing the current battery voltage (BVtoday) determined in task 310 to the low battery voltage (LowBV) determined in task 340 by referencing Table 1, and performing interpolation if the current battery voltage (BVtoday) is between two battery capacities (%) in Table 1.

The method 300 also includes a task 350 of generating an alert (e.g., sending a message from the IPG to a patient remote device) in response to the current battery voltage (BVtoday) determined in task 310 being equal to or less than the low battery voltage (LowBV) determined in task 340. The alert generated in task 350 may be any suitable type or kind of alert, such as an audio alert (e.g., a chime), a visual alert (e.g., a textual message), a tactile alert (e.g., haptic feedback), or any combination thereof.

In response to the current battery voltage (BVtoday) determined in task 310 being greater than the to the low battery voltage (LowBV), the task 350 of generating an alert is not performed and the method returns to task 305 the next time the patients wakes (e.g., the next morning). In this manner, the method 300 is configured to alert the patient sufficiently in advance of the battery losing sufficient charge to power the IPG, which could otherwise result in a serious adverse medical event.

Figure 4:
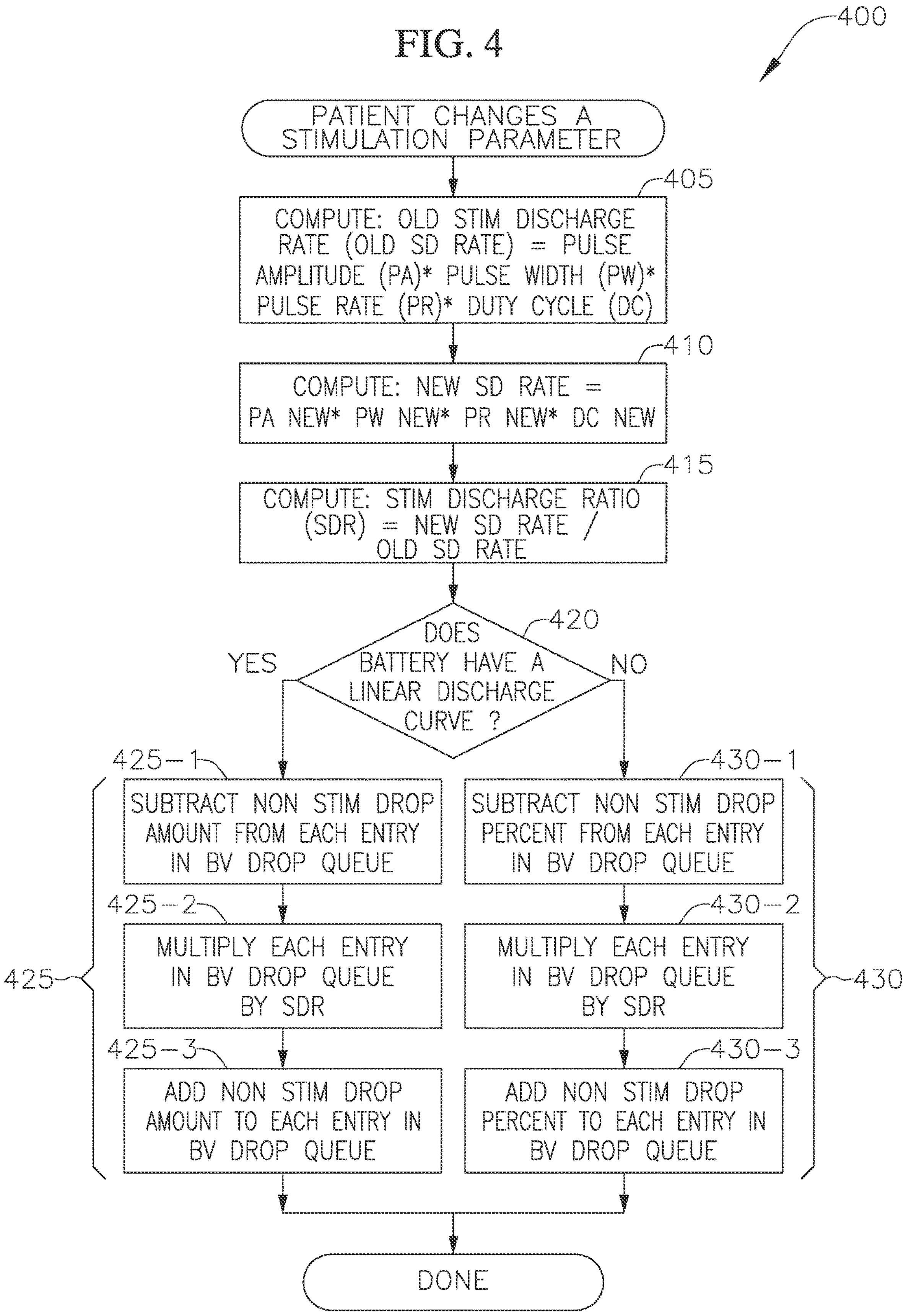
FIG. 4 is a flowchart illustrating tasks of a method of modifying the methods depicted in FIGS. 2-3 due to a change in one or more therapeutic parameters of the IPG according to one embodiment of the present disclosure.

FIG. 4 depicts a flowchart illustrating tasks of a method 400 of modifying or adjusting the task 215 of determining the average daily voltage drop (μ) of the battery in the method 200 depicted in FIG. 2, or the task 320 of determining the average daily capacity drop (μ) of the battery in the method 300 depicted in FIG. 3, in response to the therapeutic parameters (e.g., the stimulation parameters) of the IPG being changed. In one or more embodiments, one or more of the therapeutic parameters of the IPG may be adjusted by the patient or by the patient's doctor or other medical personnel to increase the therapeutic efficacy of the IPG.

In the embodiment illustrated in FIG. 4, the method 400 includes a task 405 of determining (e.g., calculating or measuring) the old stimulation discharge rate (OldSDRate) of the battery of the IPG before one or more of the therapeutic parameters of the IPG have been changed. In one or more embodiments, the old stimulation discharge rate (OldSDRate) delivered by the IPG may be calculated according to Equation 4 as follows:

$$\text{OldSDRate}=PA*PW*PR*DC \quad \text{(Equation 4)}$$

wherein PA is the amplitude of the waveform generated and delivered by the IPG to the patient, PW is the pulse width of the waveform generated and delivered by the IPG to the patient, PR is the pulse rate or frequency of the waveform generated and delivered by the IPG to the patient, and DC is duty cycle of IPG, expressed as ratio of the time that the IPG is 'on' and delivering a pulse to the patient to the time the IPG is 'off' and not delivering a pulse to the patient.

In the illustrated embodiment, the method 400 also includes a task 410 of determining (e.g., calculating or measuring) the new stimulation discharge rate (NewSDRate) of the battery of the IPG after one or more of the therapeutic parameters of the IPG have been changed. In one or more embodiments, the new average charge delivered by the IPG may be calculated according to Equation 4 as follows:

$$\text{NewSDRate}=PA_{new}*PW_{new}*PR_{new}*DC_{new} \quad \text{(Equation 5)}$$

wherein $PA_{new}$ is the amplitude of the waveform generated and delivered by the IPG to the patient after one or more of the therapeutic parameters of the IPG have been changed, $PW_{new}$ is the pulse width of the waveform generated and delivered by the IPG to the patient after one or more of the therapeutic parameters of the IPG have been changed, $PR_{new}$ iS the pulse rate or frequency of the waveform generated and delivered by the IPG to the patient after one or more of the therapeutic parameters of the IPG have been changed, and $DC_{new}$ is duty cycle of IPG, expressed as ratio of the time that the IPG is 'on' and delivering a pulse to the patient to the time the IPG is 'off' and not delivering a pulse to the patient after one or more of the therapeutic parameters of the IPG have been changed.

In the illustrated embodiment, the method 400 also includes a task 415 of determining (e.g., computing or calculating) a stimulation discharge ratio (StimDischgRatio (SDR)) of the new stimulation discharge rate (NewSDRate) of the battery of the IPG after one or more of the therapeutic parameters of the IPG have been changed, as determined in task 320, to the old stimulation discharge rate (OldSDRate) of the battery of the IPG before one or more of the therapeutic parameters of the IPG have been changed, as determined in task 310

$$\left(\text{i.e., } SDR = \frac{NewSDRate}{OldSDRate}\right).$$

As described in detail below, the SDR determined in task 415 may then be utilized to modify or adjust the average daily voltage drop (μ) of the battery determined in task 215 in the method 200 depicted in FIG. 2, or to modify or adjust the average daily capacity drop (μ) of the battery determined in task 320 of the method 300 depicted in FIG. 3.

In the illustrated embodiment, the method 400 also includes a task 420 of determining whether the battery of the IPG has linear discharge characteristics or non-linear discharge characteristics (i.e., determining whether the battery of the IPG has a linear discharge curve or not).

In response to the battery of the IPG having a linear discharge curve (i.e., "yes" in task 420), as determined in task 420, the method 400 includes a task 425 of adjusting the average daily voltage drop (μ) of the battery in the method 200 depicted in FIG. 2 before proceeding to task 225 in method 200. In the illustrated embodiment, the task 425 includes a first sub-task 425-1 of subtracting the NonStimDropAmt from each average daily voltage drop (μ) of the battery, which are stored in the queue (BVDropQueue) in the memory device of the IPG in task 220, a second sub-task 425-2 of multiplying each average daily voltage drop (μ) of the battery by the SDR calculated in task 415, and a third sub-task 425-3 of adding the NonStimDropAmt to each average daily voltage drop (μ) of the battery stored in the queue (BVDropQueue). In one or more embodiments, the NonStimDropAmt is measured or otherwise determined while stimulation is disabled (e.g., the NonStimDropAmt may be measured during development of the IPG as an average for all production boards, measured for each IPG during production, or measured for each IPG post-production).

In response to the battery of the IPG having a non-linear discharge curve (i.e., "no" in task 420), as determined in task 420, the method 400 includes a task 430 of adjusting the average daily capacity drop (μ) of the battery determined in the method 300 depicted in FIG. 3 before proceeding to task 325 in method 300. In the illustrated embodiment, the task 430 includes a first sub-task 430-1 of subtracting the Non- StimDropPct from each average daily voltage drop (μ) of the battery, which are stored in the queue (BVDropQueue) in the memory device of the IPG in task 320, a second sub-task 430-2 of multiplying each average daily voltage drop (μ) of the battery by the SDR calculated in task 415, and a third sub-task 430-3 of adding the NonStimDropPct to each average daily voltage drop (μ) of the battery stored in the queue (BVDropQueue). The NonStimDropPct may be measured or determined in the same manner as the NonStimDropAmt except it would be computed as a percentage of battery depletion instead of a number of millivolts.

The implantable pulse generator and/or any other relevant devices or components according to embodiments of the present invention described herein may be implemented utilizing any suitable hardware, firmware (e.g. an application-specific integrated circuit), software, or a combination of software, firmware, and hardware. For example, the various components of the device may be formed on one integrated circuit (IC) chip or on separate IC chips. Further, the various components of the device may be implemented on a flexible printed circuit film, a tape carrier package (TCP), a printed circuit board (PCB), or formed on one substrate. Further, the various components of the device may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the scope of the exemplary embodiments of the present invention.

Although some embodiments of the present disclosure are disclosed herein, the present disclosure is not limited thereto, and the scope of the present disclosure is defined by the appended claims and equivalents thereof.

What is claimed is:

1. A method of operating an implantable pulse generator implanted in a patient, the method comprising:

determining, by at least one processor of the implantable pulse generator, an average daily voltage depletion of a battery in the implantable pulse generator per day at a set time of day or in response to the patient waking;

determining, by the at least one processor of the implantable pulse generator, a current voltage of the battery in the implantable pulse generator;

determining, by the at least one processor of the implantable pulse generator, a depletion voltage of the battery of the implantable pulse generator associated with the battery being depleted;

transmitting, from the implantable pulse generator to an electronic device remote from the implantable pulse generator, an alert in response to the current voltage being less than a sum of the average daily voltage depletion and the depletion voltage;

detecting, by the at least one processor of the implantable pulse generator, a change in at least one stimulation parameter of the implantable pulse generator; and modifying the average daily voltage depletion based on the change in the at least one stimulation parameter.

2. The method of claim 1, further comprising determining, by the at least one processor of the implantable pulse generator, that the patient has awoken, and wherein the determining that the patient has awoken comprises:

determining, by an inertial measurement unit of the implantable pulse generator, that the implantable pulse generator is substantially vertical; and determining that the implantable pulse generator is substantially vertical for a threshold duration or at a time within a deviation of a mean or median wakeup time.

3. The method of claim 1, further comprising:

determining, by the at least one processor of the implantable pulse generator, the battery has linear discharge characteristics; and determining, by the at least one processor of the implantable pulse generator, a standard deviation of the average daily voltage depletion over a period of time, wherein the transmitting the alert is in response to the current voltage being below a sum of the average daily voltage depletion and an integer multiple of the standard deviation.

4. The method of claim 1, further comprising determining, by the at least one processor of the implantable pulse generator:

an old stimulation charge delivered by an electrode of the implantable pulse generator prior to the change in the at least one stimulation parameter;

a new stimulation charge delivered by the electrode of the implantable pulse generator after the change in the at least one stimulation parameter, wherein the determining the new stimulation charge comprises calculating a product of a pulse amplitude, a pulse width, a pulse frequency, and a duty cycle of the charge delivered by the electrode of the implantable pulse generator; and a charge ratio of the new stimulation charge to the old stimulation charge, wherein the transmitting the alert is in response to the current voltage being less than a sum of the average daily voltage depletion times the charge ratio and the depletion voltage.

5. The method of claim 4, further comprising determining, by the at least one processor of the implantable pulse generator:

an old charge consumed by the battery due to the old stimulation charge delivered by an electrode of the implantable pulse generator prior to the change in the at least one stimulation parameter;

a new charge consumed by the battery due to the new stimulation charge delivered by the electrode after the change in the at least one stimulation parameter; and a consumption ratio of the new stimulation charge consumed by the battery to the old stimulation charge consumed by the battery, wherein the transmitting the alert is in response to the current voltage being less than a sum of the depletion voltage and the average daily voltage depletion times the consumption ratio.

6. The method of claim 1, further comprising determining, by the at least one processor of the implantable pulse generator, an energy ratio of an old total energy consumed by the battery prior to the change in the at least one stimulation parameter to a new total energy consumed by the battery after the change in the at least one stimulation parameter, wherein the transmitting the alert is in response to the current voltage being less than a sum of the average daily voltage depletion times the energy ratio and the depletion voltage.

7. A method of operating an implantable pulse generator implanted in a patient, the method comprising:

determining, by at least one processor of the implantable pulse generator, a current voltage of a battery in the implantable pulse generator at a set time of day or in response to the patient waking;

determining, by the at least one processor of the implantable pulse generator, a current battery fill capacity percentage of the battery corresponding to the current voltage;

determining, by the at least one processor of the implantable pulse generator, an average fill capacity percentage drop of the battery per day over a period of time;

determining, by the at least one processor of the implantable pulse generator, a low battery voltage corresponding to the average fill capacity percentage drop;

transmitting, from the implantable pulse generator to an electronic device remote from the implantable pulse generator, an alert in response to the current voltage being less than the low battery voltage;

detecting, by the at least one processor of the implantable pulse generator, a change in a charge delivered by an electrode of the implantable pulse generator due to a change in at least one stimulation parameter of the implantable pulse generator; and modifying the average fill capacity percentage drop based on the change in the at least one stimulation parameter.

8. The method of claim 7, further comprising determining, by the at least one processor of the implantable pulse generator, that the patient has awoken, wherein the determining that the patient has awoken comprises:

determining, by an inertial measurement unit of the implantable pulse generator, that the implantable pulse generator is substantially vertical; and determining that the implantable pulse generator is substantially vertical for a threshold duration or at a time within a deviation of a mean or median wakeup time.

9. The method of claim 7, further comprising determining, by the at least one processor of the implantable pulse generator, the battery has non-linear discharge characteristics, and wherein the determining the current battery fill capacity percentage corresponding to the current voltage comprises referencing a table comprising a plurality of voltages and a corresponding plurality of battery fill capacities.

10. The method of claim 9, wherein the determining the current battery fill capacity percentage corresponding to the current voltage further comprises performing linear interpolation between two adjacent battery fill capacities of the plurality of battery fill capacities in the table.

11. The method of claim 9, further comprising generating the table and storing the table in a non-volatile memory device of the implantable pulse generator, wherein the generating the table comprises:

discharging, with a fixed resistor or a fixed current sink, the battery of the implantable pulse generator;

measuring a voltage of the battery at regular intervals during the discharging to generate the plurality of voltages; and determining the plurality of battery fill capacities corresponding to the plurality of voltages.

12. The method of claim 7, further comprising determining a standard deviation of the average fill capacity percentage drop per day over the period of time, and wherein the transmitting the alert is in response to the current voltage being less than a sum of the low battery voltage and N*the standard deviation, wherein N is an integer.

13. The method of claim 7, further comprising determining, by the at least one processor of the implantable pulse generator:

an old stimulation charge delivered by the electrode of the implantable pulse generator prior to the change in the at least one stimulation parameter;

a new stimulation charge delivered by the electrode of the implantable pulse generator after the change in the at least one stimulation parameter, wherein the determining the new stimulation charge comprises calculating a product of a pulse amplitude, a pulse width, a pulse frequency, and a duty cycle of the charge delivered by the electrode of the implantable pulse generator; and a charge ratio of the new stimulation charge to the old stimulation charge, wherein the transmitting the alert is in response to the current voltage being less than a voltage corresponding to the average fill capacity percentage drop times the charge ratio.

14. The method of claim 13, further comprising determining, by the at least one processor of the implantable pulse generator:

an old charge consumed by the battery due to the old stimulation charge delivered by the electrode;

a new charge consumed by the battery due to the new stimulation charge delivered by the electrode; and a consumption ratio of the new stimulation charge consumed by the battery to the old stimulation charge consumed by the battery, wherein the transmitting the alert is in response to the current voltage being less than a voltage corresponding to the average fill capacity percentage drop times the consumption ratio.

15. The method of claim 7, further comprising determining, by the at least one processor of the implantable pulse generator, an energy ratio of an old total energy consumed by the battery prior to the change in the at least one stimulation parameter to a new total energy consumed by the battery after the change in the at least one stimulation parameter, wherein the transmitting the alert is in response to the current voltage being less than a voltage corresponding to the average fill capacity percentage drop times the energy ratio.

16. An implantable pulse generator configured to be implanted in a patient, the implantable pulse generator comprising:

at least one processor;

a non-volatile memory device;

a communications device;

a power supply; and an inertial measurement unit, wherein the non-volatile memory device comprises instructions stored therein which, when executed by the at least one processor, cause the at least one processor to:

determine a current voltage of the power supply at a set time of day or in response to the patient being awake;

determine an average daily voltage depletion of the power supply;

transmit an alert in response to the current voltage minus the average daily voltage depletion being less than a depletion voltage of the power supply;

detect a change in at least one stimulation parameter of the implantable pulse generator; and modify the average daily voltage depletion based on the change in the at least one stimulation parameter.

17. An implantable pulse generator configured to be implanted in a patient, the implantable pulse generator comprising:

at least one processor;

a non-volatile memory device;

a communications device;

a power supply; and an inertial measurement unit, wherein the non-volatile memory device comprises instructions stored therein which, when executed by the at least one processor, cause the at least one processor to:

determine a current power supply fill capacity percentage of the power supply at a set time of day or in response to the patient being awake;

determine an average fill capacity percentage drop of the power supply per day over a period of time;

determine a low battery voltage corresponding to the average fill capacity percentage drop;

transmit an alert in response to a current voltage being less than the low battery voltage;

detect a change in a charge delivered by an electrode of the implantable pulse generator due to a change in at least one stimulation parameter of the implantable pulse generator; and modify the average fill capacity percentage drop based on the change in the at least one stimulation parameter.

* * * * *